United States Patent [19]

Liebermann et al.

[11] 4,359,579
[45] Nov. 16, 1982

[54] SYNTHESIS OF INTERMEDIATE FOR THE MANUFACTURE OF 5,6-DIHYDRO-2-METHYL-N-PHENYL-1,4-OXATHIN-3-CARBOXAMIDE

[75] Inventors: George Liebermann, Waterloo; Frederick M. M. Hager, Elmira, both of Canada

[73] Assignee: Uniroyal, Ltd., Ontario, Canada

[21] Appl. No.: 295,394

[22] Filed: Aug. 24, 1981

[30] Foreign Application Priority Data

Aug. 11, 1981 [CA] Canada .................................. 383592

[51] Int. Cl.$^3$ ............................................ C07D 327/06
[52] U.S. Cl. ...................................... 549/14; 564/202
[58] Field of Search .......................... 549/14; 564/202

[56] References Cited

U.S. PATENT DOCUMENTS

| | | | |
|---|---|---|---|
| 3,393,202 | 7/1968 | Kulka et al. | 549/14 |
| 3,399,214 | 8/1968 | Kulka et al. | 549/14 |
| 3,882,237 | 5/1975 | Knight et al. | 549/14 X |
| 4,230,871 | 10/1980 | Lee | 549/14 |

*Primary Examiner*—Richard Raymond
*Attorney, Agent, or Firm*—Marvin Bressler

[57] ABSTRACT

2-[(2-hydroxyethyl)thio]-3-oxo-N-phenylbutanamide, which is an intermediate useful in the manufacture of the fungicide, 5,6-dihydro-2-methyl-N-phenyl-1,4-oxathiin-3-carboxamide, is made by reaction of di-(2-hydroxyethyl) disulfide with acetoacetanilide in its ionized form.

10 Claims, No Drawings

SYNTHESIS OF INTERMEDIATE FOR THE MANUFACTURE OF 5,6-DIHYDRO-2-METHYL-N-PHENYL-1,4-OXATHIN-3-CARBOXAMIDE

This invention relates to the synthesis of 2-[(2-hydroxyethyl)thio]-3-oxo-N-phenylbutanamide (II) which has keto and enolic forms:

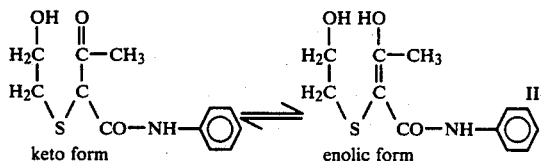

keto form          enolic form

The 2-[(2-hydroxyethyl)thio]-3-oxo-N-phenylbutanamide (II) is an intermediate in the manufacture of 5,6-dihydro-2-methyl-N-phenyl-1,4-oxathiin-3-carboxamide (I), which is a known fungicide:

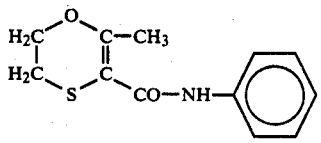

The prior art discloses a number of ways of making the fungicidal 1,4-oxathiin derivative (I). One method, disclosed in U.S. Pat. No. 3,393,202, Kulka et al., July 16, 1968, involves three steps:
1. Chlorination of acetoacetanilide to alpha-chloroacetanilide;
2. Reaction of alpha-chloroacetoacetanilide with 2-mercaptoethanol in the presence of a base to form the intermediate 2-[(2-hydroxyethyl)thio]-3-oxo-N-phenylbutanamide (II), and
3. Cyclizing the intermediate (II) under acidic conditions to form the desired 1,4-oxathiin derivative (I).

The present invention is directed to reducing the number of steps necessary to arrive at the desired final product, making possible higher overall yields, with lower material losses and lower operating costs.

In accordance with the invention, the intermediate 2-[(2-hydroxyethyl)thio]-3-oxo-N-phenylbutanamide (II) is obtained by reacting di-(2-hydroxyethyl)disulfide (III) with acetoacetanilide in an ionized form (IV) according to the following sulfenylation equation (a):

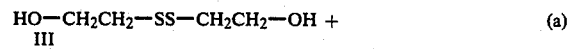

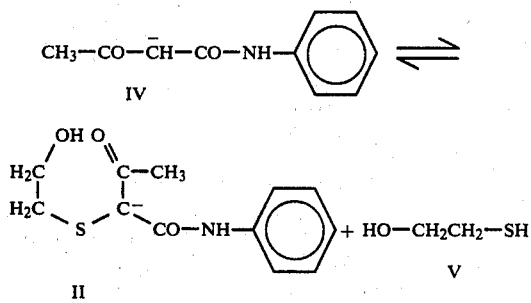

The di-(2-hydroxyethyl)disulfide (III) may be produced beforehand from 2-mercaptoethanol by air oxidation in the presence of a catalyst, or by oxidation with hydrogen peroxide. Alternatively, the di-(2-hydroxyethyl) disulfide may be produced by in situ oxidation of 2-mercaptoethanol in the sulfenylation reaction mixture.

In order to provide the ionized form (IV) of acetoacetanilide necessary for the sulfenylation reaction (a), the acetoacetanilide may be dissolved in aqueous and/or alcoholic base (e.g., NaOH or KOH). Di-(2-hydroxyethyl)disulfide (III) is added, the temperature of the reaction mixture maintained at 25°-50° C. and 2-[(2-hydroxyethyl)thio]-3-oxo-N-phenylbutanamide (II) together with 2-mercaptoethanol (V) is produced. This is an equilibrium reaction and in order to assure good conversions, the equilibrium may be shifted in the desired direction by using a slight excess of base and by oxidizing the 2-mercaptoethanol (V), in situ, to di-(2-hydroxyethyl)disulfide (III).

The intermediate (II) may be converted to the oxathiin (I) without isolation. First the reaction mixture is acidified with a suitable acid and the intermediate (II) is extracted in a solvent such as toluene or benzene. An acid catalyst such as p-toluenesulfonic acid or methanesulfonic acid is added to the organic solvent solution of (II) and the intermediate product is cyclized, usually by heating at 70°-100° C. The thus-formed 5,6-dihydro-2-methyl-N-phenyl-1,4-oxathiin-3-carboxamide (I) may be recovered from the reaction mixture by crystallization.

It will be noted that both the present method and the method proposed in U.S. Pat. No. 3,393,202 involve the same intermediate (II), which is then converted to the desired oxathiin (I). Making this intermediate in one step, instead of two, and avoiding the use of very corrosive and costly materials such as $SO_2Cl_2$ is a major advantage of the present process. No chlorinated impurities are formed in the present process, and large amounts of inorganic by-products such as $SO_2$, HCl and NaCl are also avoided.

No solvents or catalysts which are inconvenient for industrial use are required. This avoids other disadvantages of some of the prior art.

The process according the present invention is also advantageous from the point of view of raw material costs and waste problems, such as pollution control requirements or waste disposal costs.

Two main procedures can be used in carrying out the process of the invention. In the first alternative (Method A), previously prepared di-(2-hydroxyethyl) disulfide(III) is used as a raw material. In the second (Method B), 2-mercaptoethanol is used as a starting material, the conversion of 2-mercaptoethanol (V) to the disulfide (III) being performed in situ, in parallel with the progress of the sulfenylation reaction (a).

In a typical practice of Method A, acetoacetanilide (IV) is dissolved in a base, such as aqueous or/and alcoholic NaOH or KOH. The acetoacetanilide/base molar ratio is ordinarily approximately 1/1. The concentration of the resulting metal beta-diketonate solution is normally in the range of 20–60%. This solution is then put together with di-(2-hydroxyethyl) disulfide (III) and the reaction starts at temperatures of 25°-50° C. A typical disulfide/acetoacetanilide molar ratio is 1.5/1, but this can vary, depending on other reaction conditions. A slight excess of base can be used (0–20%) as this will speed up the reaction rate, however in certain conditions this excess has to be limited, as side reactions (e.g. deacetylation) can be induced. Hydrogen peroxide of 30% to 50% concentration is recommended for the in situ oxidation of 2-mercaptoethanol (V) to the disulfide (III). An excess of 0–15% $H_2O_2$ based on the theoretical 2-mercaptoethanol formed is ordinarily used. The hydrogen peroxide addition pattern follows the rate of 2-mercaptoethanol formation in the sulfenylation reaction (a). The reaction temperatures can be varied, for example from 25° C. to 55° C., with reaction times of 3.5 to 6.5 hours being typical.

After the reaction is complete, the reaction mixture is acidified with an inorganic acid, such as HCl, $H_3PO_4$ or $H_2SO_4$, and the reaction product extracted in a solvent suitable for the cyclization step, for example toluene. The solvent/intermediate (II) ratio is preferably in the range of 3 to 5/1. The aqueous phase contains the excess disulfide (III), which can be recovered and reused.

The 2-[2(hydroxyethyl)thio]-3-oxo-N-phenylbutanamide solution is subjected to cyclization using an acid catalyst, such as p-toluenesulfonic acid or methanesulfonic acid. The cyclization temperature is ordinarily maintained between 70°–100° C., usually by carrying out the reaction under vacuum. The water of reaction is conveniently removed by distillation, using one or two Dean and Stark separators.

After typically 3–5 hours of reaction, the cyclization is complete. The reaction mixture is cooled, washed with dilute NaOH, then water, and the product crystallized at low temperatures. The oxathiin (I) is then filtered and dired. The oxathiin (I) can be isolated also by removing the solvent used in the cyclization step and recrystallizing the resulting residue from another solvent, for example isopropanol.

In a modification of Method A, a suspension of acetoacetanilide (IV), disulfide (III) and water is kept under agitation while the required amount of 30–50% NaOH or KOH is added until a clear solution is obtained. The reaction mixture is heated to the desired reaction temperature, usually in the 25°–55° C. range, and the procedure is continued as described above.

In a typical practice of Method B, acetoacetanilide (IV) is dissolved in a base such as aqueous or/and alcoholic NaOH or KOH. The temperature is kept at a chosen value between 25°–55° C. and the addition of 2-mercaptoethanol (V) and hydrogen peroxide is started, following a preestablished pattern, while keeping the 2-mercaptoethanol in slight excess compared to hydrogen peroxide. A typical mole ratio of 2-mercaptoethanol/acetoacetanilide is 3/1, which corresponds to a mole ratio of di-(2-hydroxyethyl)disulfide/acetoacetanilide of 1.5/1. Hydrogen peroxide of 30 to 50% concentration is added so that the final excess is 3 to 15% molar compared with 2-mercaptoethanol, taking into account also the 2-mercaptoethanol which is forming as a result of the sulfenylation reaction (a). As the oxidation of 2-mercaptoethanol is very exothermic, appropriate cooling is needed for most of the reaction. The additions patterns are determined, depending also on other reaction conditions, so that: (1) the exothermicity can be easily controlled, (2) an excess of 2-mercaptoethanol is generally present in the reaction mixture, and (3) the pH of the reaction mixture is not lower than 10 nor higher than 12.5.

The reaction time is usually 5 to 8 hours. The work-up procedure, and the cyclization step are carried out under conditions similar to those described in Method A.

Both Method A and B can be performed using catalytic air oxidation of 2-mercaptoethanol, instead of hydrogen peroxide oxidation. In this case the reaction can be carried out at atmospheric or moderate pressures. The air flow can vary in the range of 5–50 l air/mole acetoacetanilide/hour. A standard catalyst for the oxidation of thiols, such as copper or cobalt sulphate is used in a ratio of 0.01–2.5 g/mole acetoacetanilide.

The following examples will further illustrate the practice of the invention:

EXAMPLE 1

Acetoacetanilide (88.6 g, 0.5 mole) is dissolved with agitation at room temperature in 200 g aqueous 10% NaOH (0.5 mole). Di-(2-hydroxyethyl) disulfide (120.0 g, 0.77 mole) is added, and the reaction mixture is heated to 35° C. After 15 minutes, 16 g of 15% aqueous NaOH is added, and after a further 15 minutes the continuous addition of 50% $H_2O_2$ is started. The rate of addition of hydrogen peroxide is gradually reduced as the reaction rate slows down. The hydrogen peroxide should not be, at any time, in excess of the 2-mercaptoethanol which is formed during the reaction. The 2-mercaptoethanol level is monitored by titration of a sample of acidified reaction mixture with 0.1 N iodine solution. The hydrogen peroxide addition is continued for 5 hours, maintaining the reaction temperature at 35°–37° C. A total of 16.8 g 50% $H_2O_2$ is used. The reaction mixture is cooled to 20° C., and toluene (300 g) and 5% HCl (550 g) are added with agitation. After phase separation, the toluene layer is washed three times with water. The aqueous layer and the water washes are washed two times with 100 ml toluene, in order to minimize the losses in the aqueous phase. The organic layers are combined, 0.75 g p-toluenesulfonic acid added, and the reaction mixture is cyclized at 75°–80° C., under vacuum, at reflux, with removal of the water of reaction in two Dean and Stark traps, for 3.5 hours. The reaction mixture is cooled, washed two times with 100 g 10% NaOH and three times with water. A volume reduction to approximately 400 ml is performed, by removing some of the toluene by evaporation. The toluene solution is then allowed to crystallize overnight at a temperature below −10° C. After filtration and drying, 75.8 g 5,6-dihydro-2-methyl-N-phenyl-1,4-oxathiin-3-carboxamide is obtained (Yield 64.5% based on acetoacetanilide). M.P. 90.8°–97.8°, Assay 98.0%.

EXAMPLE 2

Acetoacetanilide (88.6 g, 0.5 mole) is dissolved under agitation, at room temperature, in 140 g aqueous 28.6% NaOH (0.5 mole). Crude di-(2-hydroxyethyl) disulfide (176 g), obtained by oxidation of 2-mercaptoethanol with 50% hydrogen peroxide, (i.e. an approx 68% aqueous solution) is added to the reaction mixture, which is then heated to 38° C. After 15 minutes 15% aqueous NaOH (16 g) is added and after a further 15 minutes the addition of 50% hydrogen peroxide is started. Subsequently the reaction is carried out as described in EXAMPLE 1. A total of 16.8 g 50% hydrogen peroxide is used. The extraction/acidification procedure, as well as the cyclization step, is carried out as in EXAMPLE 1. After the last water wash, following the cyclization, toluene is evaporated from the reaction mixture under vacuum, at up to 60°, and the residue is redissolved in 90 g isopropanol. After crystallization, filtration and drying, 80.2 g 5,6-dihydro-2-methyl-N-phenyl-1,4-oxathiin- 3-carboxamide is obtained (yield 68.1% based on acetoacetanilide), M.P. 96.8°–98.0° C., Assay 98.9%.

EXAMPLE 3

A suspension of acetoacetanilide 88.6 g (0.5 mole) and 68% aqueous di-(2-hydroxyethyl) disulfide (176.0 g) is stirred and 50% aqueous NaOH (40 g) is added dropwise so that the temperature does not increase above 40° C. and a clear solution results. The temperature of the reaction mixture is maintained at 35°–38° C. for 15 minutes, then an additional 8 g of 15% aqueous NaOH is added. After a further 15 minutes, the addition of 50% hydrogen peroxide is started. Subsequently, the reaction is carried out as in EXAMPLE 1. A total of 17.6 g 50% $H_2O_2$ is used.

The extraction/acidification step is carried out as in EXAMPLE 1 using 5% HCl (560 g). The cyclization step and the work-up of the crude reaction product are carried out as in EXAMPLE 1. 5,6-Dihydro-2-methyl-N-phenyl-1,4-oxathiin-3-carboxamide (80.8 g) is obtained. (Yield 68.7% based on acetoacetanilide) M.P. 96.8°–97.6° C., Assay 98.6%.

EXAMPLE 4

Acetoacetanilide (88.6 g, 0.5 mole) is dissolved under agitation, at room temperature, in 140 g aqueous 28.6% NaOH (0.5 mole). The temperature is adjusted to 35° C., and the additions of 2-mercaptoethanol (120.0 g) and 50% $H_2O_2$ (56.4 g) started. 2-Mercaptoethanol (10 ml) is added before starting the hydrogen peroxide addition, and a slight molar excess of 2-mercaptoethanol is maintained till the end, so that this addition is finished approximately 15 minutes bofore that of hydrogen peroxide. The additions are carried out in 2 hours, with cooling of the reaction mixture, and maintaining the temperature between 34° and 38° C. 15% Aqueous NaOH (16 g) is added to the reaction mixture, followed by 17 g 50% $H_2O_2$ during 4 hours while keeping the temperature at 35°–38° C.

This procedure is then continued as in EXAMPLE 1 and the product is recrystallized from isopropanol as in EXAMPLE 2. Yield of 5,6-dihydro-2-methyl-N-phenyl-1,4-oxathiin-3 carboxamide is 75.6 g (64.3% based on acetoacetanilide). M.P. 98°–98.8° C., Assay 99.4%.

EXAMPLE 5

A suspension of acetoacetanilide (88.6 g, 0.5 mole) in 68% aqueous di-(2-hydroxyethyl) disulfide (170.0 g) and water (150 g) is stirred and 50% aqueous NaOH (41.6 g) is added so that the temperature does not increase above 40° C. and a clear solution results. The temperature of the reaction mixture is maintained at 35° C. for 30 minutes. 1.0 g $CuSO_4.5H_2O$ is added and the air flow is started through a fine porosity dispersion disk at a rate of 250 ml/minute for 5 hours, maintaining the reaction temperature at 35°–37° C.

The extraction/acidification procedure, cyclization step and the work up of the batch to the finished product, are carried out as in EXAMPLE 1.

5,6-Dihydro-2-methyl-N-phenyl-1,4-oxathiin-3-carboxanilide (81.6 g) is obtained (yield 69.4% based on acetoacetanilide), Assay 98.6%.

What is claimed is:

1. A method for making 5,6-dihydro-2-methyl-N-phenyl-1,4-oxathiin-3-carboxamide by cyclization of the intermediate 2-[(2-hydroxyethyl)thio]-3-oxo-N-phenyl-butanamide, in which this intermediate is obtained by the reaction of di-(2-hydroxyethyl) disulfide with acetoacetanilide.

2. A method for making 2-[(2-hydroxyethyl)thio]-3-oxo-N-phenylbutanamide comprising reacting di-(2-hydroxyethyl) disulfide with acetoacetanilide in an ionized form.

3. A method as in claim 2 in which the di-(2-hydroxyethyl) disulfide is preformed before being added to the reaction mixture.

4. A method as in claim 2 in which the di-(2-hydroxyethyl)disulfide is formed in situ in the reaction mixture.

5. A method as in claim 4 in which the di-(2-hydroxyethyl)disulfide is formed in situ by adding 2-mercaptoethanol and oxidizing same with hydrogen peroxide or air.

6. A method as in claim 2 in which the acetoacetanilide is dissolved in aqueous and/or alcoholic base.

7. A method as in claim 2 in which the reaction mixture is maintained at a temperature in the range of from 25° to 50° C.

8. A method as in claim 2 in which the equilibrium is shifted toward the desired product by employing an excess of base and by oxidizing by-product 2-mercaptoethanol in situ to di-(2-hydroxyethyl) disulfide with hydrogen peroxide or air.

9. A method as in claim 2 in which the molar ratio of acetoacetanilide to base is approximately 1/1, the concentration of the obtained beta-diketonate base is in the range of from 20 to 60%, the disulfide/acetoacetanilide molar ratio is 1.5/1, and a 0–15% excess of 30–50% hydrogen peroxide is added based on the theoretical 2-mercaptoethanol formed.

10. A method as in claim 2 in which the reaction mixture is an aqueous solution which is acidified and extracted with an organic solvent at the completion of the reaction to remove the 2-[(2-hydroxyethyl)thio]-3-oxo-N-phenylbutanamide product, and excess di-(2-hydroxyethyl)disulfide remaining in the aqueous phase is recycled.

* * * * *